United States Patent [19]
Bradburn

[11] Patent Number: 6,091,834
[45] Date of Patent: Jul. 18, 2000

[54] METHOD OF ILLUMINATING A DIGITAL REPRESENTATION OF AN IMAGE

[75] Inventor: Graham Bradburn, Herts, United Kingdom

[73] Assignee: Fujifilm Electronic Imaging, Limited, Herts, United Kingdom

[21] Appl. No.: 09/200,906

[22] Filed: Nov. 27, 1998

Related U.S. Application Data

[62] Division of application No. 08/880,164, Jun. 20, 1997, abandoned.

[30] Foreign Application Priority Data

Jun. 28, 1996 [GB] United Kingdom ............... 9613685

[51] Int. Cl.$^7$ .............................. G06T 5/00; G06T 7/40; H04N 1/409
[52] U.S. Cl. ................. 382/108; 382/275; 250/559.02; 250/559.07; 250/559.14; 250/559.41; 250/559.45; 356/239; 358/463
[58] Field of Search ................................ 382/275, 254, 382/270, 108, 112; 358/463, 475, 480; 356/237, 239; 250/559.02, 559.07, 559.16, 559.4, 559.41, 559.45

[56] References Cited

U.S. PATENT DOCUMENTS

| | | |
|---|---|---|
| 3,920,311 | 11/1975 | Tsuda et al. . |
| 4,410,278 | 10/1983 | Makihira et al. .................. 250/559.07 |
| 4,568,984 | 2/1986 | Juergensen et al. .................... 358/293 |
| 4,626,101 | 12/1986 | Ogawa et al. ........................... 356/237 |
| 4,989,973 | 2/1991 | Noso et al. ............................. 356/239 |
| 5,058,982 | 10/1991 | Katzir . |
| 5,315,405 | 5/1994 | Okuwaki ................................. 358/445 |
| 5,517,575 | 5/1996 | Ladewski ............................... 382/108 |
| 5,625,719 | 4/1997 | Fast et al. ............................... 382/275 |
| 5,742,395 | 4/1998 | Biedermann et al. .................. 356/237 |
| 5,883,714 | 3/1999 | Jann et al. .............................. 356/237 |

FOREIGN PATENT DOCUMENTS

| | | |
|---|---|---|
| 0 097 724 A1 | 6/1982 | European Pat. Off. . |
| 0 678 910 A2 | 10/1995 | European Pat. Off. . |
| 24 41 822 | 6/1975 | Germany . |
| WO 93/13406 | 7/1993 | WIPO . |

*Primary Examiner*—Scott Rogers
*Attorney, Agent, or Firm*—Sughrue, Mion, Zinn, Macpeak & Seas, PLLC

[57] ABSTRACT

An illumination unit for positioning adjacent a record medium support surface of an analyze scanner on which a record medium to be scanned is positioned in use. The unit comprises a housing with a slot extending at least partially along its length. At least one radiation source is supported within the housing, whereby a beam of radiation passes through the slot. A radiation absorbing surface is provided offset from the radiation source so as to form a background when viewing the slot through the medium support surface in a direction offset to the beam direction.

24 Claims, 4 Drawing Sheets

METHOD OF ILLUMINATING A DIGITAL REPRESENTATION OF AN IMAGE

This is a divisional of application Ser. No. 08/880,164 filed Jun. 20, 1997, the disclosure of which is incorporated herein by reference.

FIELD OF INVENTION

The invention relates to apparatus and methods for detecting and/or reducing the effect of imperfections in an image contained on a record medium mounted on an analyse scanner.

DESCRIPTION OF PRIOR ART

In a typical analyse scanner for generating an electronic representation of an image, the images on a record medium are mounted on a record medium supporting surface such as a transparent drum or flat bed using a variety of methods. In each method it is necessary to ensure that there are no dust particles, scratches or oil bubbles present in the area of image to be scanned. In the past effectiveness of the mounting was determined by visual inspection of the mounted image, however under normal illumination such imperfections are difficult to identify.

Once the imperfections have been identified, some of them such as dust can simply be removed, however there are many applications where such a solution does not result in a sufficiently perfect image or an automatic procedure for dealing with imperfections is preferred. One example is where an image recorded on a record medium needs to be digitized for subsequent processing, storage, output and the like. Conventionally, this is achieved by scanning the record medium, sensing light emitted from the record medium and impinging on an imaging lens, and then digitizing the received light pixel by pixel. If imperfections such as scratches are present, then the light impinging on the imperfection is scattered away from the imaging lens resulting in a dark streak being produced in the image. These dark scratches are then permanently recorded within the digitized image. In the past, this has been dealt with either by using air brush techniques or by using a diffuse source to illuminate the transparency from all directions. The problem with the first approach is that it is time consuming and requires skill by the operator to recognize and deal with the scratches while the second approach is very light inefficient.

One approach for estimating the surface condition of a plate object is described in U.S. Pat. No. 4,989,973. Light is directed towards the plate object and a sensor located out of the path of the light produces an electrical signal in response to light of diffused reflection from the plate object. An estimate of the surface condition of the plate object is obtained by reference to the diffused reflection. In practice, it is difficult to sense accurately the diffused light.

U.S. Pat. No. 3,920,311 describes a microscope illuminator to facilitate observation of objects within the field of view of the microscope objective. It is not concerned with the detection of imperfections.

U.S. Pat. No. 5,058,982 describes a system for inspecting opaque objects by reflection.

EP-A-0678910 describes an illumination device for illuminating the surface of a semiconductor disc enclosed by a hemispherical cover. This allows fully automised quality control.

WO 93/13406 illustrates apparatus for discriminating defects on the surface of an optical recording medium such as an optical memory card. The system works under reflection.

SUMMARY OF THE INVENTION

In accordance with a first aspect of the present invention there is provided a method for detecting imperfections in a surface of a record medium support or a record medium mounted thereon, the method comprising illuminating the support surface with a beam of radiation from a source, the support being transparent to the radiation, viewing the support surface against a radiation absorbing surface offset from the radiation source, the viewing directing being at an angle offset to the direction in which the illuminating beam impinges on the support surface, the beam of radiation having passed through the support, and determining the presence of imperfections by detecting regions with an enhanced brightness.

We have devised a new method for observing imperfections in a mounted record medium, in the record medium support surface itself or between the medium and the medium support surface. The method involves providing illumination that impinges on the support surface, at an angle offset to the direction in which the surface is viewed. If a region of the scanner surface containing no imperfections is viewed along the viewing direction, then the method ensures that the direct light rays from the radiation source(s) will be out of the line of sight of the observer and the region will appear substantially dark. However, if imperfections are present in the medium, or the medium support surface, or between them, then the light rays will be scattered into the line of sight of the observer. As a result, the observed region will appear substantially dark with areas of enhanced brightness that correspond to the imperfections.

It should be realised that such a method may be implemented in a variety of different ways. For example the procedure could be manual in which the support is viewed by the naked eye or alternatively the method could be automated in which the viewing means could be a scanning system of some form.

In either case, it would be possible to view the support surface at an angle offset to the normal and provide normal illumination although typically the radiation impinges on the record medium support surface at an angle offset to the normal to the surface and the surface is viewed along the normal. This allows for easier orientation and observation of the surface.

The radiation absorbing surface may take a variety of forms but preferably absorbs substantially all wavelengths generated by the beam source. In the case of visible wavelengths, the radiation absorbing surface is preferably black or dark blue.

Furthermore, it would be possible to use a variety of radiation sources, although it is possible to use apparatus in accordance with a second aspect of the present invention in which there is provided an illumination unit for positioning adjacent a record medium support surface of an analyse scanner on which a record medium to be scanned is positioned in use, the unit comprising a housing with a slot extending at least partially along its length; at least one radiation source supported within the housing, whereby a beam of radiation passes through the slot; and a radiation absorbing surface offset from the radiation source so as to form a background when viewing the slot through the medium support surface in a direction offset to the beam direction.

The radiation source for providing the illumination may be either a light emitting diode, a light bulb, or a semiconductor laser, but preferably the radiation source is a fluorescent tube. This has the advantage that it provides an extended source of illumination. Thus, when positioned relative to the image support surface, a single tube is able to provide light rays along the length of the support surface, rather than requiring the use of multiple sources.

Typically, the unit will also consist of a radiation shield for forming the radiation into a beam, although the radiation beam could also be produced using a focusing means such as a curved mirror or lens. The use of a shield provides a much simpler construction than would be possible were a focusing means to be used.

To aid observation of the imperfections, the radiation absorbing surface is preferably incorporated into the radiation shield. This allows simpler construction than if the shield and screen were separate.

The radiation shield may be located anywhere within the housing but it is preferably positioned within the housing, opposite the slot, with the background surface facing the slot. This provides the background against which the scanner surface or record medium is observed.

The image support surface can be a flat surface, such as in a flat bed scanner, or a cylindrical drum, as in an analyse cylinder scanner.

The housing could be of any shape desired, however the housing is typically a tube. This enables it to be easily inserted either under a flat mounting surface or into a cylindrical drum.

The illumination could be provided by a single source but typically the unit comprises at least two radiation sources which are preferably supported symmetrically about a plane passing through the centre of the slot and the axis of the tube. The use of two symmetrically mounted sources means that light rays from two different directions are incident on the imperfections. This has the advantages that more radiation is scattered, hence making the imperfections appear brighter when observed and it ensures that the imperfections are more evenly illuminated.

This apparatus provides illumination that allows the method according to the first aspect of the present invention to be carried out. Once the imperfections have been detected, it is possible to remove some of them, such as dust, by hand. Despite this, some imperfections may remain and these can be dealt with by implementing a further automatic procedure. Alternatively an automatic method may be preferred over the manual method in some circumstances, for example if a large number of images were to be handled in a short time period.

To allow imperfections to be dealt with automatically, we have provided, in accordance with a third aspect of the present invention, a method of generating a digital representation of an image on a record medium, the method comprising
 a) illuminating the medium in a first manner to cause radiation from the medium to impinge on a sensing device which generates a first digital representation of the appearance of the medium;
 b) illuminating the medium in a second manner such that radiation from imperfections on the medium has enhanced brightness in comparison with radiation from other parts of the medium and causing the radiation to impinge on the sensing device to generate a second digital representation of the appearance of the medium; and,
 c) modifying the first digital representation to remove the effect of the imperfections by reference to the second digital representation to generate a digital representation of the image.

In accordance with a fourth aspect of the present invention, apparatus for generating a digital representation of an image on a record medium, the apparatus comprising a record medium support on which a record medium can be positioned; means for illuminating the medium on the support with radiation; a sensing device for sensing radiation from a medium on the support and for generating a digital representation of the appearance of the medium under illumination; and processing means connected to the sensing device, the apparatus being adapted to carry out a method according to the first aspect of the invention.

We have also devised a new method and apparatus for automatically dealing with imperfections on a record medium either in conjunction with or independently of either the first or second aspects of the present invention. The process is achieved essentially by illuminating the medium in two different manners, firstly so that the medium is generally equally illuminated and secondly so that the imperfections are highlighted. The two illumination manners could be achieved by using separate light sources or by using a single source which is moved from one position to another. In particular, the second manner of illumination can be achieved by offsetting the light source in such a way that light scattered by the imperfections only is received by an imaging lens or by utilising an illumination unit according to the second aspect of the present invention.

Step c) could be carried out in a variety of ways. In a very simple approach, the second digital representation, possibly after a suitable weighting modification, could be added to the first digital representation.

In a more sophisticated approach, the second digital representation is processed to form a mask which identifies the location of the imperfections, the first digital representation then being modified under the control of the mask to eliminate the effect of imperfections. This modification could be an interpolation or replication technique, or an artistic method, such as an electronic air brush technique, using the mask as a guide to highlight defective parts of the original.

The generation of a mask could be carried out by using a thresholding technique. For example, by comparing each stored pixel value with a predetermined threshold or automatically by calculating a threshold which may also be variable across the image area or by using some other algorithm designed to select out defects from the background.

This second approach is preferred to the first because during step b) it is possible that part of the image will still be sensed by the sensing device and this may need to be eliminated. For example, in the case of a transparency, the transparency emulsion also scatters light and thus will generate an additional faint reproduction of the image on the transparency.

Steps (a) and (b) can be performed in any order or simultaneously by alternatively strobing the two illuminating sources during a single scan.

Although the third and fourth aspects could be implemented with opaque record media, preferably the medium is transparent, the medium being illuminated from one side and the sensing device being positioned to detect radiation emitted from the other side.

The processing means could be in the form of separate hardware components, a suitably programmed computer or a combination of the two.

The record medium could comprise a positive or negative which will preferably be scanned in a first manner under transmitted light. Scanning of the record medium in the second manner could be achieved using either transmitted or reflected light.

The illumination source(s) will typically generate light in the visible wavelength range but it would also be possible to operate at wavelengths outside the visible wavelength range in certain situations.

Typically, two sources will be provided but in some cases more than two sources could be used in order to achieve a rapid, full scan of the record medium, or a single movable source. In general the radiation will comprise visible light but it could comprise wavelengths outside the visible range e.g. UV or infrared.

BRIEF DESCRIPTION OF THE DRAWINGS

Some examples of apparatus and methods according to the invention will now be described with reference to the accompanying drawings, in which.

DETAILED DESCRIPTION OF THE EMBODIMENTS

Figure 1:
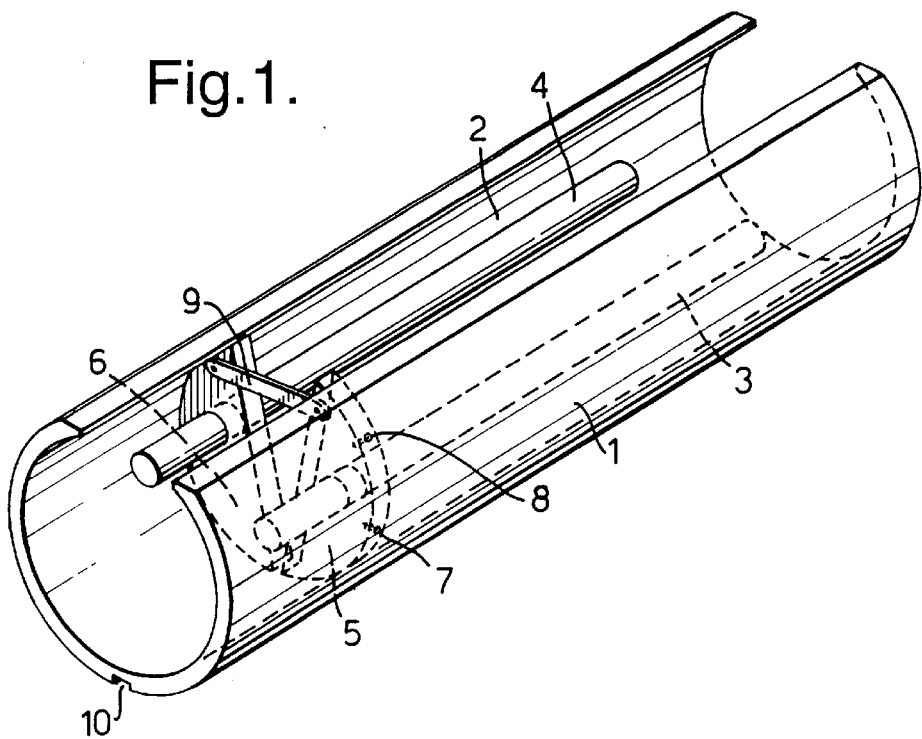
FIG. 1 is a perspective view of an illumination unit.
Figure 2:
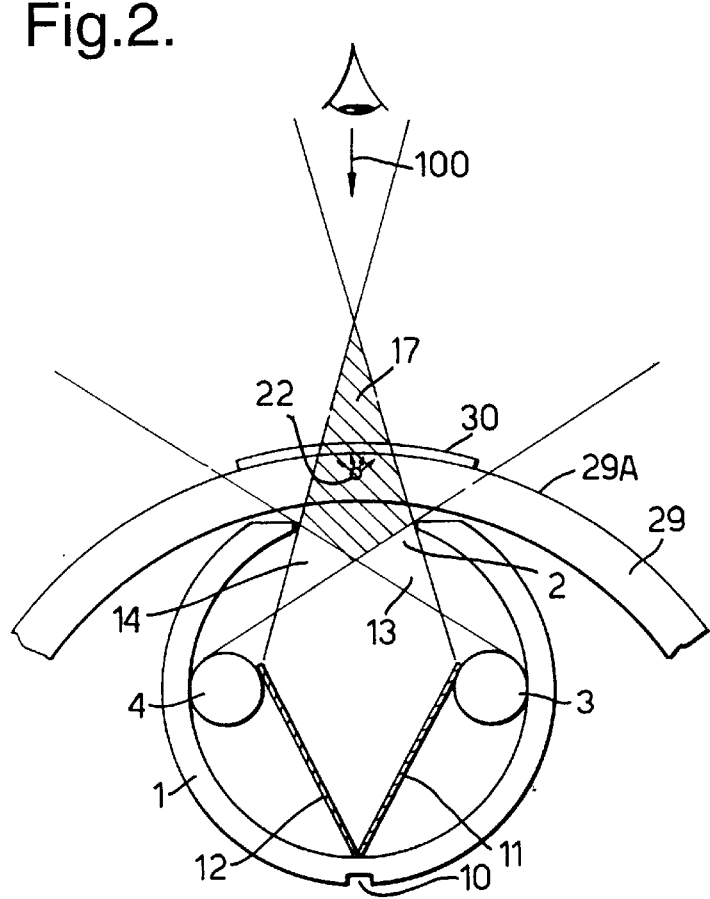
FIG. 2 is a cross-sectional view of the unit shown in FIG. 1 when mounted in an analyse scanner drum.
Figure 3:
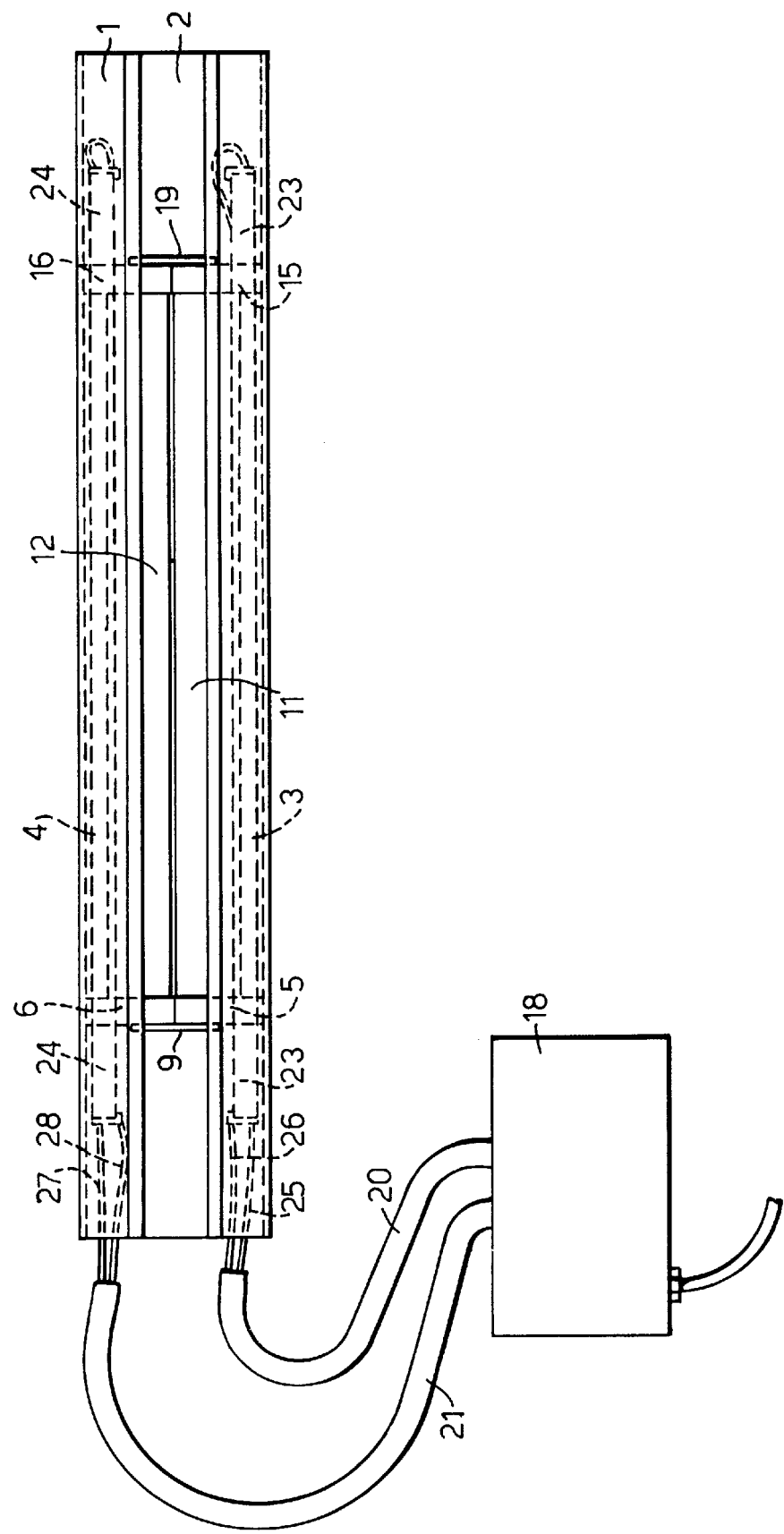
FIG. 3 is a plan view of the unit shown in FIG. 1.

The apparatus shown in FIGS. 1 to 3 comprises an opaque tube 1 having a length of about 800 mm and a diameter of about 85 mm with a slot 2, having a length of about 450 mm and a width of about 30 mm, extending along the tube's length. Located inside the tube 1, and parallel to the tube axis, are two laterally spaced fluorescent tubes 3 and 4. These are held in place by almost semi-circular fixtures 5 and 6. In the preferred embodiment two additional fixtures 15,16 are also included to support the other ends of the fluorescent tubes 3,4. The fixture 5 is held in place by screws 7 and 8 extending through the tube 1. Similar screws (not shown) are used to hold the remaining fixtures 6,15,16 in position.

To prevent the tube 1 collapsing in on itself, a pair of support struts 9 and 19 extend laterally between respective pairs of fixtures 5,6 and 15,16. A rectangular groove 10 in the outer surface of the tube 1 is positioned opposite the slot 2 to increase the flexibility of the tube. This facilities the adjustment of the slot width. Different struts 9,19 will be used depending on the chosen slot width.

The unit also includes a pair of radiation shields 11 and 12, shown in FIG. 2 but omitted from FIG. 1. These block direct radiation from the fluorescent tubes 3,4 passing through the slot 2 and, in conjunction with the slot 2, define two radiation beams 13 and 14. The beams pass through the slot 2 and intersect to form an area of maximum illumination 17.

In the preferred embodiment the tube 1 and the shields 11 and 12 are blackened to absorb any radiation emitted by the fluorescent tubes 11,12 which falls on them. The blackened shields 11,12 provide a background against which a support surface and a transparency can be viewed.

FIG. 3 shows a plan view of the illumination unit. This highlights the fact that when looking towards the tube 1, at an angle normal to the plane of the slot 2, only the blackened shielding 11,12 is visible through the slot. The radiation shields 11,12 are located mid-way along the tube 1, with fixtures 5 and 6 at one end, and fixtures 15 and 16 at the other.

The fluorescent tubes 3,4 are mounted through holes in the fixtures 5,6,15,16 such that the ends of the tubes project from the outer ends of the fixtures. The projecting ends 23,24 of the tubes 3,4 respectively are blackened to absorb the radiation. This prevents unwanted illumination of the support surface which would reduce the effectiveness of the unit.

The tubes 3,4 are connected to an electrical power source 18, via leads 20 and 21. Each lead consists of two wires 25,26 and 27,28 respectively. The leads 20 and 21 enter the tube 1 at one end, where a respective wire 25,27 from each lead 20,21 is connected to one of the tubes 3,4. The remaining wires 26,28 pass behind the radiation shields 11,12 and are connected to the other ends of the fluorescent tubes 3,4.

To carry out an example of the method of the present invention the unit is inserted inside a drum 29 of an analyse scanner (FIG. 2) and may be held in position adjacent to the record medium support surface 29A by some supporting means or brackets (not shown) or the unit may be hand held allowing the user to position the unit as required. It should be noted that the use of a cylindrical drum scanner is not meant to be limiting and the apparatus will work equally well with a flat bed scanner. The drum may, or may not, have a transparency 30 mounted upon it. The unit is positioned so that the region of the drum to be checked for imperfections 22 falls within the area of maximum illumination 17. The region can then be inspected by an observer looking toward the slot 2, along a viewing direction.

Generally the preferred viewing direction is along the normal to the support surface 29A, in which case the light beams impinge on the drum surface at an angle offset to the viewing direction. Furthermore, the light sources 3,4 are concealed from the observer by the edge of the slot 2. As a result, an observer looking along the viewing direction 100 will not have any direct rays of radiation incident upon their eye. Thus, when viewed against a black background, the drum and transparency appear substantially dark.

It is possible that the analyse scanner drum 29 may contain imperfections 22 such as scratches or dirty marks. The mounted transparency will also be subject to imperfections including dust and scratches, while oil bubbles may be formed between the scanner surface 29A and the transparency 30, if the transparency is oil mounted. Light rays incident upon these imperfections 22 will be scattered. Some of the scattered rays will then be incident upon the eye of the observer.

As a result, the observed region will appear uniformly dark with areas of enhanced brightness. These areas correspond to the position of the imperfections, in either the drum or the transparency. An example of the appearance of a typical transparency appearance is shown in FIG. 4.

Figure 4:
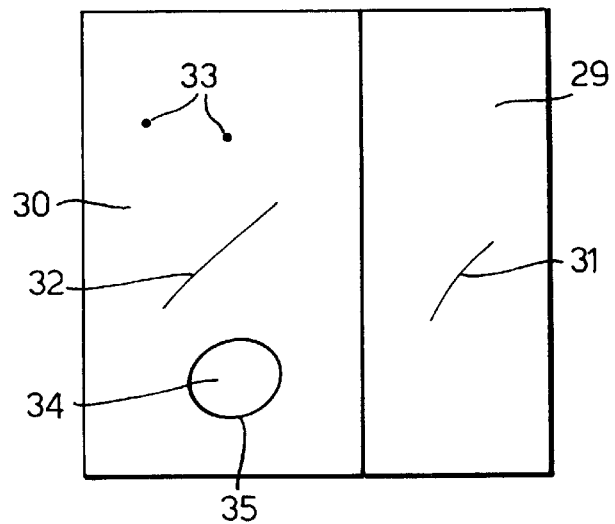
FIG. 4 is a representation of a typical image viewed using the illumination unit.

FIG. 4 represents the image seen by someone making a visual inspection of a transparency 30, mounted on a scanner drum 29. The image can be considered as a negative image in that when observed, the drum 29 and transparency 30 would appear substantially dark with areas of increased brightness, rather than substantially light with areas of reduced brightness.

Markings 31 and 32 represent the images seen as a result of scratches in the drum 29 and transparency 30, respectively. Any particles of dust will scatter light rays from a point, and hence the dust particles will be observable as points of illumination 33. Finally, the presence of an oil bubble between the transparency 30 and drum surface 29, will cause the formation of a slightly brighter region 34, surrounded by an even brighter perimeter 35. The brighter perimeter is the result of increased scattering at the oil forming the edge of the bubble.

It should be noted that the invention is not restricted to visual inspection, it is also possible to use the illumination unit in conjunction with alternative detection means, such as a light sensitive scanner. If the device were used with a scanner, then it would also be possible to use non-visible illumination, for example infra-red radiation. In this instance it would be necessary to ensure that the scanner is capable of detecting the wavelength of radiation used for illuminating the drum surface.

Once the imperfections have been detected, it is possible to remove some of them. This can be performed in a variety of ways and depends largely upon the type of imperfection. For example, dust on the surface of the medium support or the record medium could be removed by cleaning the surface. Oil bubbles present between the medium and the support surface could be reduced by remounting or applying pressure to that region to disperse the collected oil. Furthermore, should the support surface be scratched, it may be necessary to replace it.

Figure 5:
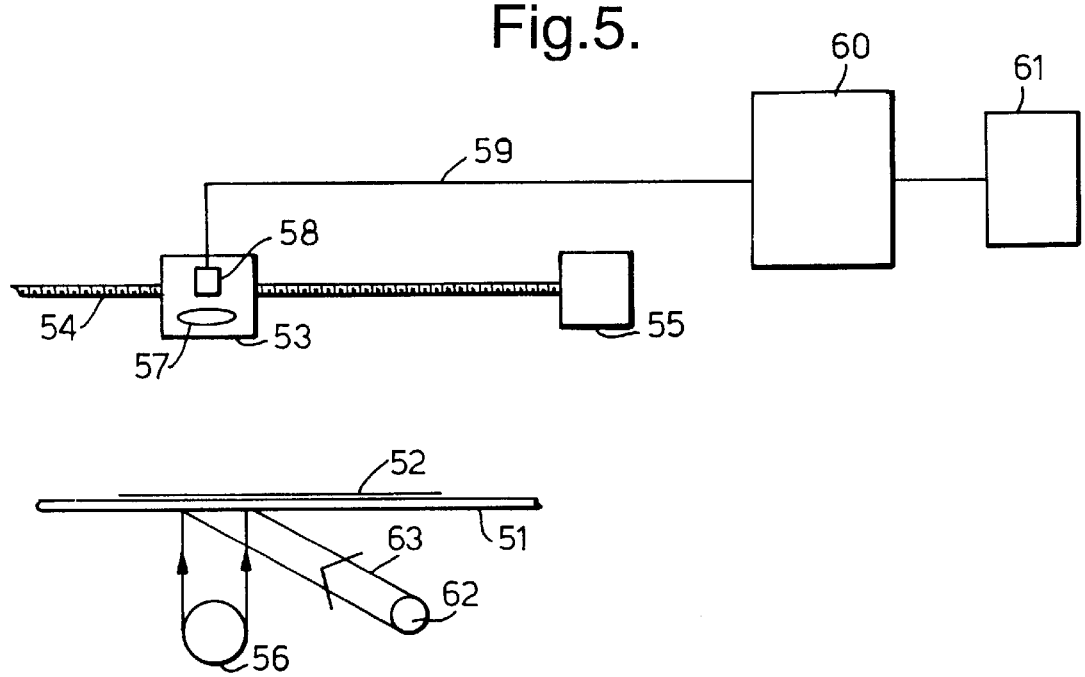
FIG. 5 is a schematic, block diagram of an apparatus used to reduce the effects of the imperfections; and, FIG. 6 is a flow diagram illustrating operation of the apparatus shown in FIG. 5.

Apparatus to enable imperfections to be compensated is shown in FIG. 5 and comprises a record medium support 51 such as a transparent cylinder or flat bed. A transparency 52 to be imaged is secured on the surface of the support 51. Positioned above the support 51 is a scanning head 53 mounted to a lead screw 54 which is rotated by a motor 55. Beneath the support 51 is positioned a first light source 56. Alternatively, the support 51 could define a gap over which the transparency is located.

The record medium support 51 is movable to cause the transparency 52 to be scanned in a first direction beneath the head 53, the first direction being orthogonal to a second direction along which the head 53 moves upon rotation of the lead screw 54. The source 56 is mounted so as to move with the head 53. In this way, the entire transparency 52 can be scanned by the scanning head 53.

The scanning head 53 includes an imaging lens 57 mounted beneath a light or radiation detector 58. The detector 58 receives light which has passed through the transparency 52 (and been modulated by the image on the transparency 52). Electrical signals obtained from the detector 58 are passed along a line 59 to a processor 60. The processor 60 digitizes the signals and passes them to a store 61 where a value is stored for each pixel of the transparency 52 representing the intensity of received light.

In this example, we have described the scanning of a black and white image but the invention is also applicable to coloured images in which case the scanning head 3 would be modified suitably in a conventional manner.

Finally, an auxiliary light source 62 is provided which generates a beam 63 which is offset from a vertical axis extending through the transparency 52 from the head 53. Whilst this source may simply be an offset source as shown in FIG. 5, it would also be possible to use the illumination unit of FIG. 1 to provide the so called offset illumination, providing the fluorescent tubes 3,4 can be separately actuated.

The operation of the apparatus shown in FIG. 5 will now be described.

Figure 6:
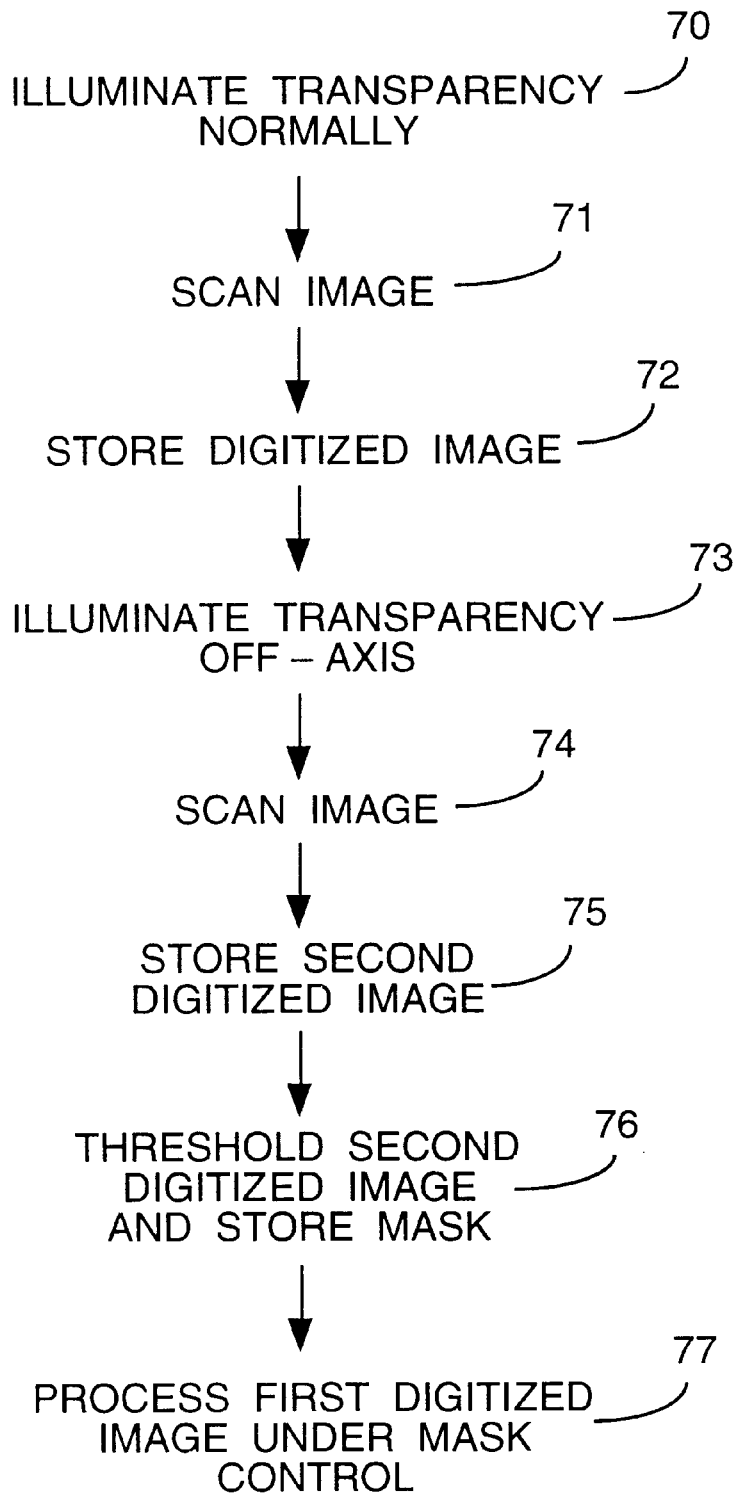

Initially, the transparency 52 is mounted on the support 51 and the source 56 is activated. The source 62 remains deactivated. The source 56 illuminates the transparency 52 beneath the head 53 in a generally even manner (step 70, FIG. 6) and light from a small area of the transparency 52 is focused by the lens 57 onto the CCD detector 58. The detector may be any suitable detector such as a CCD detector array the form of which will be well known to people skilled in the art. The lead screw 54 is rotated to cause the scanning head 53 to move along the lead screw under control of the motor 55 (with corresponding movement of the source 56) while the support 51 is moved in an orthogonal direction. In this way, all parts of the transparency 52 are imaged onto the CCD detector 58 (step 71). The signal from the detector 58 is downloaded along the line 59 to the processor 60 where it is digitized and then stored in appropriate locations in the store 61 corresponding to the respective pixels (step 72).

The light source 56 is then deactivated and the light source 62 activated. Light from the source 62 impinges on the transparency 52 at an acute angle so that substantially only light diffracted or refracted by imperfections such as scratches on the transparency 52 will be directed to the imaging lens 57. It is possible also that the emulsion on the transparency 52 will also cause some light scatter but this will in general be much fainter than light scattered by the scratches. (Step 73). The transparency 52 is again scanned (step 74), the source 62 moving with the head 53, and a second digitized image of the appearance of the transparency 52 is stored in the store 61 (step 75).

The image could be compared with a predetermined intensity threshold set so as to be exceeded only by the intensity of light expected from imperfections such as scratches. A mask image is then generated in which each pixel contains a single binary value "0" or "1" indicating the absence or presence respectively of sufficient light to indicate a scratch.

The processor 60 then uses the mask image to locate scratches in the first digitized image and replaces the stored value in a pixel identified by a "1" in the mask image with an interpolated value based on adjacent pixels. (step 77). In this way the effects of scratches in the first image are removed.

In the example shown, two sources 56,62 are used. In other cases, it would be possible to mount the source 56 on a movable cradle so that it could be adjusted from the position shown to the position of the source 62.

I claim:

1. A method of generating a digital representation of an image on a record medium, the method comprising:

a) illuminating said medium in a first manner to cause radiation from said medium to impinge on a sensing device which generates a first digital representation of the appearance of said medium;

b) illuminating said medium in a second manner such that radiation from imperfections on said medium has enhanced brightness in comparison with radiation from other parts of said medium and causing said radiation to impinge on the sensing device to generate a second digital representation of the appearance of said medium; and, c) modifying said first digital representation to remove the effect of said imperfections by reference to said second digital representation to generate a digital representation of the image;

wherein c) includes generating a value in said first digital representation for each pixel corresponding to an imperfection by a method of interpolation or replication.

2. A method according to claim 1, wherein c) comprises adding said second digital representation to said first digital representation, if necessary after said second digital representation has been weighted in a preliminary step.

3. A method according to claim 1, wherein c) comprises generating a mask from said second digital representation, and modifying said first digital representation with reference to said mask.

4. A method according to claim 3, wherein said mask is generated by comparing each stored pixel value with a predetermined threshold.

5. A method according to claim 1, wherein said radiation comprises visible light.

6. A method according to claim 1, wherein said a) and b) are carried out sequentially.

7. A method according to claim 1, wherein said medium is transparent, said medium being illuminated from one side and said sensing device being positioned to detect radiation emitted from the other side.

8. A method according to claim 1, wherein said record medium comprises a transparency or photographic negative.

9. A method according to claim 1, wherein in a) said medium is illuminated normally and in b) said medium is illuminated in an off-normal direction.

10. A method according to claim 1, wherein said radiation comprises visible light.

11. A method according to claim 1, wherein said a) and b) are carried out sequentially.

12. A method of generating a digital representation of an image on a record medium, the method comprising:
   a) illuminating said medium in a first manner to cause radiation from said medium to impinge on a sensing device which generates a first digital representation of the appearance of said medium;
   b) illuminating said medium in a second manner such that radiation from imperfections on said medium has enhanced brightness in comparison with radiation from other parts of said medium and causing said radiation to impinge on the sensing device to generate a second digital representation of the appearance of said medium; and,
   c) modifying said first digital representation to remove the effect of said imperfections by reference to said second digital representation to generate a digital representation of the image;
wherein in a) said medium is illuminated normally and in b) said medium is illuminated in an off-normal direction.

13. A method according to claim 12, wherein c) comprises adding said second digital representation to said first digital representation, if necessary after said second digital representation has been weighted in a preliminary step.

14. A method according to claim 12, wherein c) comprises generating a mask from said second digital representation, and modifying said first digital representation with reference to said mask.

15. A method according to claim 14, wherein said mask is generated by comparing each stored pixel value with a predetermined threshold.

16. A method according to claim 12, wherein said medium is transparent, said medium being illuminated from one side and said sensing device being positioned to detect radiation emitted from the other side.

17. A method according to claim 12, wherein said record medium comprises a transparency or photographic negative.

18. A method according to claim 12, wherein c) includes generating a value in said first digital representation for each pixel corresponding to an imperfection by a method of interpolation or replication.

19. Apparatus for generating a digital representation of an image on a record medium, the apparatus comprising a record medium support surface on which a record medium can be positioned; means for illuminating said medium on said support with radiation; a sensing device for sensing radiation from a medium on said support and for generating a digital representation of the appearance of the medium under illumination; and processing means connected to said sensing device, the apparatus being adapted to carry out the following:
   a) illuminating said medium in a first manner to cause radiation from said medium to impinge on a sensing device which generates a first digital representation of the appearance of said medium;
   b) illuminating said medium in a second manner such that radiation from imperfections on said medium has enhanced brightness in comparison with radiation from other parts of said medium and causing said radiation to impinge on the sensing device to generate a second digital representation of the appearance of said medium; and,
   c) modifying said first digital representation to remove the effect of said imperfections by reference to said second digital representation to generate a digital representation of the image;
wherein c) includes generating a value in said first digital representation for each pixel corresponding to an imperfection by a method of interpolation or replication.

20. Apparatus according to claim 19, wherein two light sources are provided for illuminating said medium in said first and second manners respectively.

21. Apparatus according to claim 19, wherein said light source for illuminating the medium in the second manner is provided by an illumination unit comprising a housing defining a slot extending at least partially along its length; at least one radiation source supported within said housing, whereby a beam of radiation passes through said slot; and a radiation absorbing surface offset from said radiation source so as to form a background when viewing the slot through the medium support surface in a direction offset to the beam direction.

22. Apparatus for generating a digital representation of an image on a record medium, the apparatus comprising a record medium support surface on which a record medium can be positioned; means for illuminating said medium on said support with radiation; a sensing device for sensing radiation from a medium on said support and for generating a digital representation of the appearance of the medium under illumination; and processing means connected to said sensing device, the apparatus being adapted to carry out the following:
   a) illuminating said medium in a first manner to cause radiation from said medium to impinge on a sensing device which generates a first digital representation of the appearance of said medium;
   b) illuminating said medium in a second manner such that radiation from imperfections on said medium has enhanced brightness in comparison with radiation from other parts of said medium and causing said radiation to impinge on the sensing device to generate a second digital representation of the appearance of said medium; and,
   c) modifying said first digital representation to remove the effect of said imperfections by reference to said second digital representation to generate a digital representation of the image;

wherein in a) said medium is illuminated normally and in b) said medium is illuminated in an off-normal direction.

23. Apparatus according to claim 22, wherein two light sources are provided for illuminating said medium in said first and second manners respectively.

24. Apparatus according to claim 22, wherein said light source for illuminating the medium in the second manner is provided by an illumination unit comprising a housing defining a slot extending at least partially along its length; at least one radiation source supported within said housing, whereby a beam of said radiation passes through said slot; and a radiation absorbing surface offset from said radiation source so as to form a background when viewing the slot through the medium support surface in a direction offset to the beam direction.

* * * * *